United States Patent [19]

Scott

[11] 4,370,335
[45] Jan. 25, 1983

[54] ANTISECRETORY 4-DIPHENYLMETHYL-1-[(OXOALKYL-)IMINO]METHYL-PIPERIDINES AND THEIR DERIVATIVES

[75] Inventor: Malcolm K. Scott, Ambler, Pa.

[73] Assignee: McNeilab, Inc., Fort Washington, Pa.

[21] Appl. No.: 345,128

[22] Filed: Feb. 2, 1982

[51] Int. Cl.³ .................. A61K 31/445; C07D 405/12
[52] U.S. Cl. .................................. 424/267; 546/192; 546/207; 546/226; 546/232; 546/235
[58] Field of Search ............ 546/235, 232, 207; 424/267

[56] References Cited

U.S. PATENT DOCUMENTS

| 3,946,022 | 3/1976 | Carr et al. | 546/235 X |
| 4,077,976 | 3/1978 | Bulteau et al. | 546/235 X |
| 4,251,655 | 2/1981 | Scott et al. | 546/232 X |

*Primary Examiner*—Richard A. Schwartz

[57] ABSTRACT

4-Diphenyl-1-[(oxo and oxo-related alkyl)imino]methyl-piperidine derivatives are disclosed which are useful for the inhibition of gastric acid secretion.

10 Claims, No Drawings

ANTISECRETORY 4-DIPHENYLMETHYL-1-[(OXOALKYL)IMINO]-METHYL-PIPERIDINES AND THEIR DERIVATIVES

BACKGROUND OF THE INVENTION

This invention relates to 4-diphenylmethyl-1-[(oxoalkyl)-imino]methyl-piperidine derivatives and more particularly to those compounds of Formula II below and their pharmaceutically acceptable acid addition salts, which are inhibitors of gastric acid secretion.

PRIOR ART

The compounds of the present invention are the oxo or related derivatives of certain compounds disclosed in U.S. Pat. No. 4,251,655, such as 4-diphenylmethyl-1-[octylimino]methyl piperidine which has the formula:

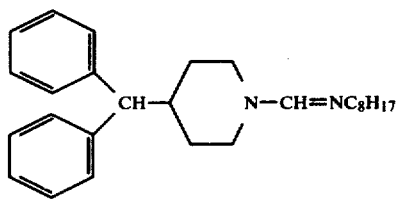
(I)

SUMMARY OF THE INVENTION

The present invention is concerned with 4-diphenylmethyl-1-[(oxoalkyl)-imino]methylpiperidines and their derivatives of the following Formula II, and pharmaceutically acceptable acid addition salts thereof:

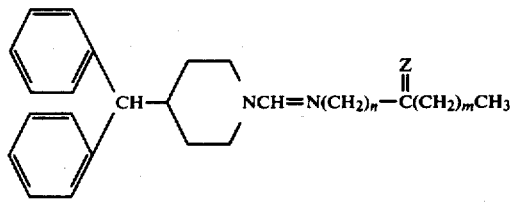
(II)

wherein:
n is an integer from 1–10, inclusive
m is an integer from 0–9, inclusive
n+m=1–10
Z is selected from the following:

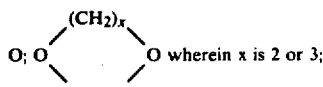 wherein x is 2 or 3;

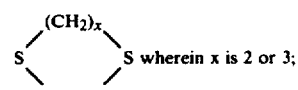 wherein x is 2 or 3;

$(OR_1)_2$ wherein $R_1$ is $C_{1-6}$ loweralkyl; NOH; and H,OH.

The compounds of the present invention all have an oxo or ketone function, or a function related thereto such as an —OH (which may be considered as a reduced ketone), or an oxime=N—OH, or a ketal

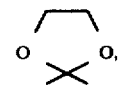

or thioketal

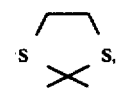

or acetal $(OR_1)_2$.

As used herein, the term "loweralkyl" refers to both straight chain and branched chain alkyls, e.g., methyl, ethyl, propyl, isopropyl, t-butyl, hexyl, and the like.

METHODS OF PREPARATION

The compounds of the present invention may be prepared by the following reaction scheme:

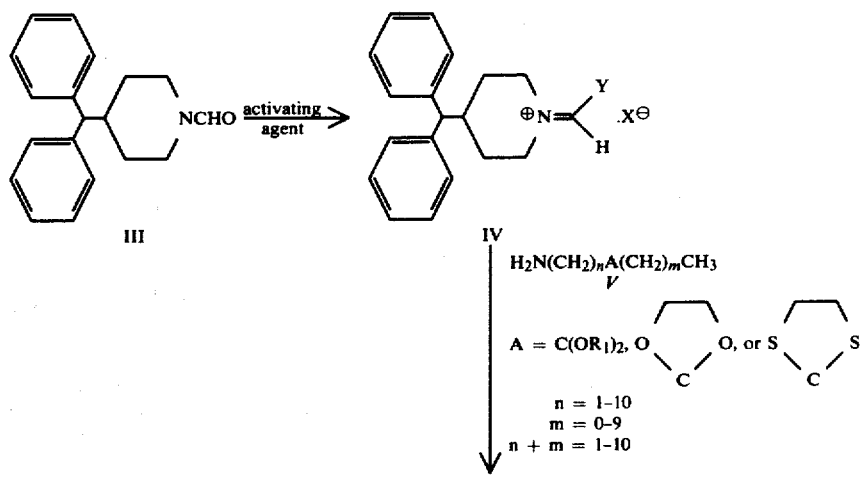

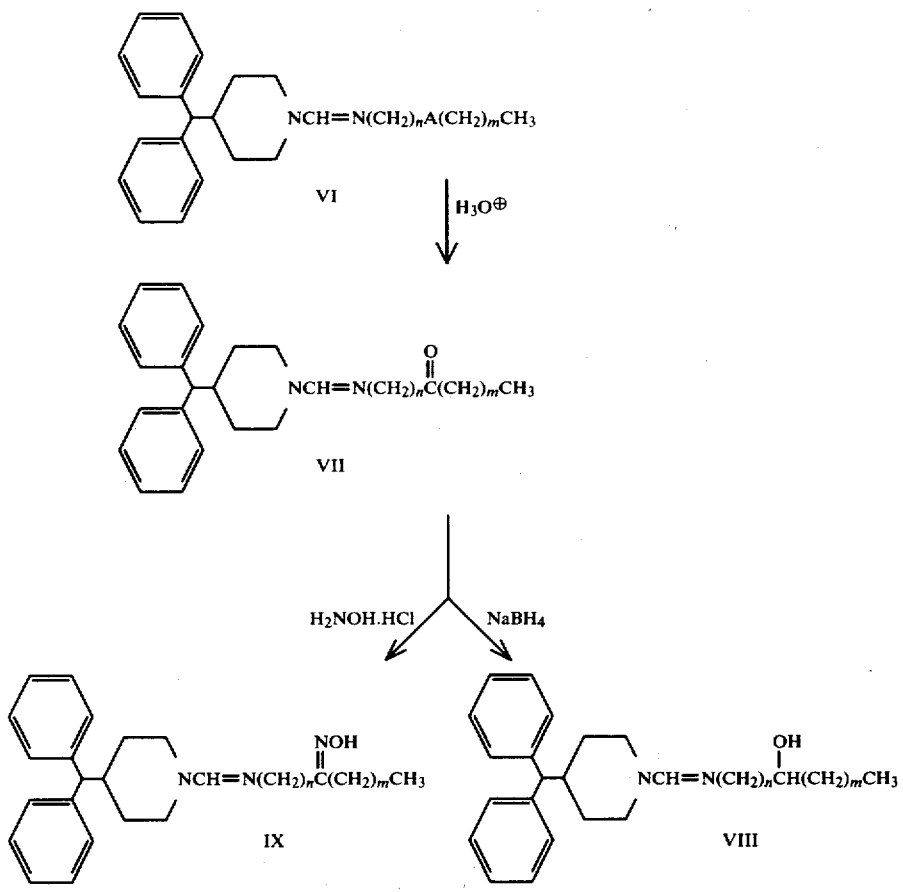

An appropriately activated derivative (IV) of N-formyl-4-(diphenylmethyl)piperidine (III), prepared from III and an activating agent chosen from, for example, phosgene (preferred), $Me_3O^+BF_4^-$, $Et_3O^+BF_4^-$, $(MeO)_2SO_2$, $MeOSO_2F$, $POCl_3$, $PCl_5$ and the like may be treated with an appropriate primary amine of general structure V to give an amidine of general structure VI. Amidine VI is treated with aqueous acid to obtain a keto amidine of general structure VII. Reduction of VII to the alcohol of general structure VIII may be accomplished with sodium borohydride as the reducing agent. Oximes of general structure IX are prepared by treating VI with hydroxylamine hydrochloride.

Because the subject compounds (II) possess a basic amidine group, they may be converted into the corresponding acid addition salts.

The acid addition salts may be prepared by reaction with an appropriate acid, as for example an inorganic acid such as a hydrohalic acid, i.e., hydrochloric, hydrobromic or hydroiodic acid; sulfuric or nitric acid; phosphoric acid; an organic acid such as acetic, propionic, glycolic, pamoic, pyruvic, oxalic, malonic, succinic, maleic, picric, fumaric, malic, tartaric, citric, benzoic, cinnamic, mandelic, methanesulfonic, ethanesulfonic, benzenesulfonic, p-toluenesulfonic, salicylic, 2-naphthalenesulfonic or p-aminosalicylic acid. The therapeutically active, nontoxic acid addition salts of subject compounds (II) and their hydrates or solvates are included within the scope of the present invention.

The starting materials may be prepared by known methods or as illustrated in detail in the Preparations section.

METHOD OF TESTING

The compounds of the invention are useful for inhibition of gastric acid secretion as measured by the following test. Female Sprague-Dawley rats are fasted twenty-four hours before testing and are given water ad libidum while being kept in individual cages. On the day of testing, the rats are weighed and are selected so that the rats in each test weigh within a range ±20 grams.

Surgery is carried out under light ether anesthesia. As soon as the rat is anesthetized its teeth are removed and a mid-line incision is made on the abdomen about 1½ inches in length and the stomach and duodenum are exposed. If at this point the stomach is filled with food or fecal material, the rat is discarded. If the condition of the stomach is acceptable, a purse string stitch is placed on the fundic portion of the stomach with a suture, taking care not to pierce any blood vessels in the area. A small nick is then made into the stomach in the center of the purse string, and a cannula, consisting of a small vinyl tube with a flange on one end, is put into the stomach, and the purse string stitch is closed tightly around the flange. The test compound is administered either intraduodenally (i.d.) immediately after surgery or orally (p.o.) one hour prior to surgery at doses generally ranging from about 0.25 to about 160 mg/kg in a volume of 0.5 ml/100 grams rat. Control rats receive the test vehicle, 0.5% aqueous methyl cellulose.

After the surgery and (in the case of i.d. administration) after administration of the test compound, the abdominal wall and skin are closed simultaneously with three or four 18 mm wound clips and a collecting tube is placed on the cannula. Each rat is then placed in a box in which a longitudinal slit has been made to allow the cannula to hang freely and to allow the rat to move about unencumbered. After the rat has been allowed to stabilize for thirty minutes, the collection tube on the cannula is discarded and replaced with a clean tube to receive the gastric juice. Collections are made at one hour. At the end of the study, the cannula is removed and the rat is sacrificed.

The sample of gastric contents collected is drained into a centrifuge tube and centrifuged to pack down the sediment. The volume is read and a 1 ml aliquot of the supernatant is put into a beaker containing 10 ml distilled water and is titrated to pH 7 using 0.01 N sodium hydroxide. Results are determined for Volume, Titratable Acid and Total Acid Output, where Volume equals total ml of gastric juice minus sediment; Titratable Acid (meq/l) equals amount of 0.01 N sodium hydroxide needed to titrate the acid to pH 7; and Total Acid Output equals Titratable Acid times Volume. Results are reported as the $ED_{50}$ dose (mg/kg required to produce an average of 50% inhibition in Total Acid Output versus controls in all the animals tested for a particular compound) and as percent inhibition. The compounds of the invention all demonstrate a significant inhibition both i.d. and p.o. at less than 80 mg/kg, with preferred compounds having an $ED_{50}$ p.o. less than 20 mg/kg.

It is well-known that excessive secretion of gastric hydrochloric acid leads to unneeded peptic activity and endangers the mucous lining of the stomach. The use of gastric antisecretory agents is thus desirable as an aid in the prevention and amelioration of distress occasioned by high concentrations of stomach acid.

The results obtained for representative compounds of the invention by the above test for inhibition of gastric secretion are shown in Table I:

TABLE I

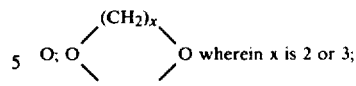

| Compound of Example No. | n | X | $ED_{50}$ Acute Gastric Fistula, Rat (mg/kg p.o.) |
|---|---|---|---|
| 1 | 4980-46-98 | 6 | O(CH$_2$)$_2$O | 3.14 |
| 2 | 4955-46-98 | 6 | O | 14.74 |
| 3 | 4978-71-98 | 6 | H,OH | 78.08 |
| 4 | 5085-71-98 | 6 | NOH | 12.31 |
| 5 | 5066-46-98 | 8 | O | 4.76 |
| 6 | 5020-11-98 | 1 | O | 6.07 |

DESCRIPTION OF THE PREFERRED EMBODIMENTS

The compounds within the scope of the invention are those of Formula II wherein:
n is 1–10
m is 0–9; n+m is 1–10
Z is selected from the following:

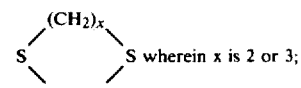

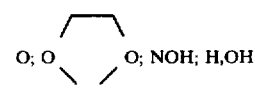

(OR$_1$)$_2$ wherein R$_1$ is C$_{1-6}$ loweralkyl; NOH; and H,OH.

The preferred compounds are those of Formula II wherein:
n is 1–10
m is 0–9; n+m is 1–10
Z is selected from the following:

O; O⟨O⟩O; NOH; H,OH and the most preferred compounds are those in Table I.

DESCRIPTION OF THE METHOD OF TREATMENT AND PHARMACEUTICAL COMPOSITIONS

In view of the antisecretory activity of the subject compounds, there is further provided herein a method of inhibiting gastric acid secretion which comprises internally administering to a gastric hyperacidic subject (man or animal) an effective gastric acid secretion inhibiting amount of a substituted N-iminomethylpiperidine of Formula (II), in base or acid addition salt form, preferably in admixture with a pharmaceutically acceptable carrier. If an acid addition salt form is used, said salt must of course be pharmaceutically-acceptable and non-toxic. Pharmaceutical compositions comprising a subject compound (II) are also considered a further aspect of the present invention.

To prepare the pharmaceutical compositions of the present invention, a substituted N-iminomethylpiperidine of Formula (II) or an acid addition salt thereof is combined as the active ingredient in intimate admixture with a pharmaceutical carrier according to conventional pharmaceutical compounding techniques, which carrier may take a wide variety of forms depending on the form of preparation desired for administration, e.g., oral or parenteral. In preparing the compositions in oral dosage form, any of the usual pharmaceutical media may be employed, such as for example, water, glycols, oils, alcohols, flavoring agents, preservatives, coloring agents, and the like in the case of oral liquid preparations such as for example, suspensions, elixirs, and solutions; or carriers such as starches, sugars, diluents, granulating agents, lubricants, binders, disintegrating agents, and the like in a case of oral solid preparations, such as for example, powders, capsules, and tablets. Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, although other ingredients, for example, to aid solubility or for preservative purposes, may be included. Injectable suspensions may also be prepared, in which case appropriate liquid carriers, suspending agents, and the like may be employed. The pharmaceutical compositions herein will contain, per dosage unit, e.g., tablet, capsule, powder, injection, teaspoonful, and the like, from about ten to about 500 milligrams of the active ingredient, and preferably from about fifteen to about 250 milligrams.

The following preparations, showing how to prepare various starting materials and examples are intended to illustrate but not to limit the scope of the present invention.

PREPARATION OF STARTING MATERIALS

Preparation 1

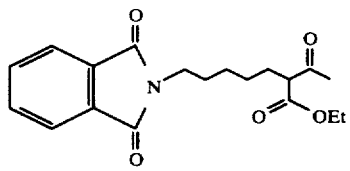

N-[7-Oxo(6-carboethoxy)octyl]phthalimide

A solution of sodium ethoxide in ethanol, prepared by dissolving 23.69 g (1.03 moles) of sodium in 800 ml of absolute alcohol, was treated slowly with ethyl acetoacetate. To this solution was added, in one portion, 308 g (1.04 moles) of N-(5-bromopentyl)phthalimide and the resulting mixture was refluxed for two hours and stirred overnight at 25°. The ethanol was stripped, 1500 ml of water was added to the residue, and the resulting mixture was extracted with 3×400 ml of ether. The ether layers were combined, dried over anhydrous sodium sulfate, filtered and stripped to give 350 g of light brown oil. This material was used in the next step without purification.

Preparation 2

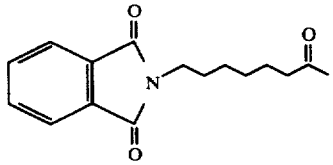

N-(7-Oxooctyl)phthalimide

A mixture of 350 g of crude N-[7-oxo(6-carboethoxy)octyl]phthalimide and 1000 ml of acetic acid, concentrated hydrochloric acid, and water was refluxed for three hours. The reaction mixture was stripped, the residue dissolved in methylene chloride and basified with 2 N NaOH solution. The organic layer was separated, dried over anhydrous sodium sulfate, filtered and stripped to an orange oil, 73% pure by gc (SE-30, 90-280°@16°/min). This material was used without further purification in Preparation 3.

Preparation 3

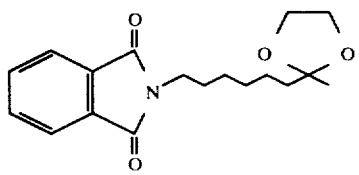

N-[6-(2-Methyl-1,3-dioxolan-2-yl)hexyl]phthalimide

A mixture of 142.0 g (0.52 mole) of N-(7-oxooctyl)phthalimide, 60 ml of ethylene glycol, 5.80 g of p-toluenesulfonic acid and 290 ml of benzene was refluxed overnight using a Dean-Stark trap to collect the azeotrope. The reaction was cooled, treated with 2 N NaOH solution, the organic layer separated, dried over anhydrous potassium carbonate, filtered and stripped to give 125.25 g of orange oil, 76% pure by gc (SE-30, 90°-280°@16°/min).

Preparation 4

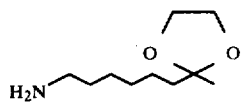

N-[6-(2-Methyl-1,3-dioxolan-2-yl)hexyl]amine

A mixture of 125.25 g (0.395 mole) of N-[6-(2-methyl-1,3-dioxolan-2-yl)hexyl]phthalimide, 23 ml of 85% hydrazine hydrate, and 370 ml of 95% ethanol was refluxed for four hours, cooled, filtered and stripped. The residue was mixed with 500 ml of water, basified with 2 N NaOH solution and extracted with methylene chloride. The organic layer was separated, dried over anhydrous potassium carbonate, filtered, and stripped to an orange oil. This material was distilled to give 35.70 g (64%) of clear oil bp 80°-83° (0.100 mm).

Preparation 5

Following the procedure described in Preparation 1 and using the appropriate N-bromoalkylphthalimides and β-ketoesters, the following can be prepared:

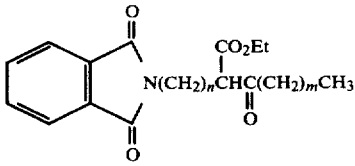

| n | m |
|---|---|
| 5 | 4 |
| 4 | 3 |
| 3 | 2 |
| 2 | 1 |
| 9 | 0 |
| 7 | 0 |
| 4 | 0 |
| 3 | 0 |
| 2 | 0 |

Preparation 6

Following the procedure described in Preparation 2 the following can be prepared:

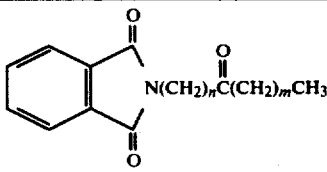

| n  | m |
|----|---|
| 6  | 4 |
| 5  | 3 |
| 4  | 2 |
| 3  | 1 |
| 10 | 0 |
| 9  | 0 |
| 7  | 0 |
| 5  | 0 |
| 4  | 0 |
| 3  | 0 |

Preparation 7

Following the procedure described in Preparation 3 the following can be prepared:

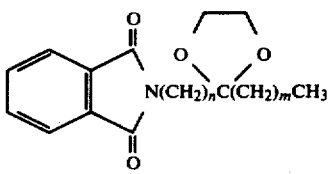

| n  | m |
|----|---|
| 6  | 4 |
| 5  | 3 |
| 4  | 2 |
| 3  | 1 |
| 10 | 0 |
| 9  | 0 |
| 7  | 0 |
| 5  | 0 |
| 4  | 0 |
| 3  | 0 |

Preparation 8

Using the procedure described in Preparation 7, but substituting various carbinols for ethylene glycol, the following acetals may be prepared:

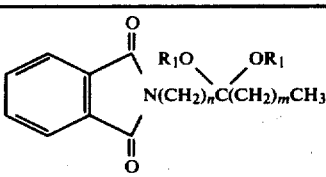

| n  | m | $R_1$ |
|----|---|-------|
| 6  | 4 | $CH_3-$ |
| 5  | 3 | $CH_3-$ |
| 4  | 2 | $CH_3-$ |
| 3  | 1 | $CH_3-$ |
| 10 | 0 | $CH_3-$ |
| 9  | 0 | $CH_3-$ |

-continued

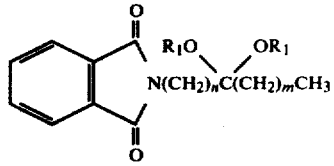

| n  | m | $R_1$ |
|----|---|-------|
| 8  | 0 | $CH_3-$ |
| 7  | 0 | $CH_3-$ |
| 6  | 0 | $CH_3-$ |
| 5  | 0 | $CH_3-$ |
| 4  | 0 | $CH_3-$ |
| 3  | 0 | $CH_3-$ |
| 6  | 4 | $CH_3CH_2-$ |
| 5  | 3 | $CH_3CH_2-$ |
| 4  | 2 | $CH_3CH_2-$ |
| 3  | 1 | $CH_3CH_2-$ |
| 10 | 0 | $CH_3CH_2-$ |
| 9  | 0 | $CH_3CH_2-$ |
| 8  | 0 | $CH_3CH_2-$ |
| 7  | 0 | $CH_3CH_2-$ |
| 6  | 0 | $CH_3CH_2-$ |
| 5  | 0 | $CH_3CH_2-$ |
| 4  | 0 | $CH_3CH_2-$ |
| 3  | 0 | $CH_3CH_2-$ |

Preparation 9

Following the procedure described in Preparation 4, the following can be prepared:

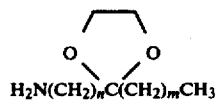

| n  | m |
|----|---|
| 6  | 4 |
| 5  | 3 |
| 4  | 2 |
| 3  | 1 |
| 10 | 0 |
| 9  | 0 |
| 7  | 0 |
| 5  | 0 |
| 4  | 0 |
| 3  | 0 |
| 1  | 6 |
| 1  | 5 |
| 1  | 3 |

Preparation 10

Using the procedure described in Preparation 4, the following amino ketals can be prepared:

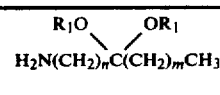

| n  | m | $R_1$ |
|----|---|-------|
| 6  | 4 | $CH_3-$ |
| 5  | 3 | $CH_3-$ |
| 4  | 2 | $CH_3-$ |
| 3  | 1 | $CH_3-$ |
| 10 | 0 | $CH_3-$ |
| 9  | 0 | $CH_3-$ |
| 8  | 0 | $CH_3-$ |
| 7  | 0 | $CH_3-$ |
| 6  | 0 | $CH_3-$ |
| 5  | 0 | $CH_3-$ |

-continued

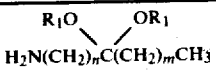

| n | m | $R_1$ |
|---|---|---|
| 4 | 0 | $CH_3-$ |
| 3 | 0 | $CH_3-$ |
| 1 | 6 | $CH_3-$ |
| 1 | 5 | $CH_3-$ |
| 1 | 3 | $CH_3-$ |
| 1 | 0 | $CH_3-$ |
| 6 | 4 | $CH_3CH_2-$ |
| 5 | 3 | $CH_3CH_2-$ |
| 4 | 2 | $CH_3CH_2-$ |
| 3 | 1 | $CH_3CH_2-$ |
| 10 | 0 | $CH_3CH_2-$ |
| 9 | 0 | $CH_3CH_2-$ |
| 8 | 0 | $CH_3CH_2-$ |
| 7 | 0 | $CH_3CH_2-$ |
| 6 | 0 | $CH_3CH_2-$ |
| 5 | 0 | $CH_3CH_2-$ |
| 4 | 0 | $CH_3CH_2-$ |
| 3 | 0 | $CH_3CH_2-$ |
| 1 | 6 | $CH_3CH_2-$ |
| 1 | 5 | $CH_3CH_2-$ |
| 1 | 3 | $CH_3CH_2-$ |
| 1 | 0 | $CH_3CH_2-$ |

Preparation 11

Following the method of Fieser, J. Am. Chem. Soc., 76, 1945 (1954) and using the compounds of Preparations 2 and 6 and ethanedithiol the following may be prepared:

| n | m |
|---|---|
| 6 | 4 |
| 5 | 3 |
| 4 | 2 |
| 3 | 1 |
| 1 | 0 |
| 10 | 0 |
| 9 | 0 |
| 8 | 0 |
| 7 | 0 |
| 6 | 0 |
| 5 | 0 |
| 4 | 0 |
| 3 | 0 |
| 1 | 6 |
| 1 | 5 |
| 1 | 4 |
| 1 | 3 |

Preparation 12

Using the method of Preparation 9, the following can be prepared:

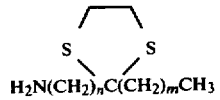

| n | m |
|---|---|
| 1 | 3 |

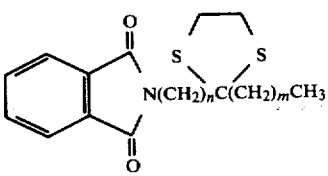

| n | m |
|---|---|
| 6 | 4 |
| 5 | 3 |
| 4 | 2 |
| 3 | 1 |
| 1 | 0 |
| 10 | 0 |
| 9 | 0 |
| 8 | 0 |
| 7 | 0 |
| 6 | 0 |
| 5 | 0 |
| 4 | 0 |
| 3 | 0 |
| 1 | 6 |
| 1 | 5 |
| 1 | 4 |
| 1 | 3 |

EXAMPLE 1

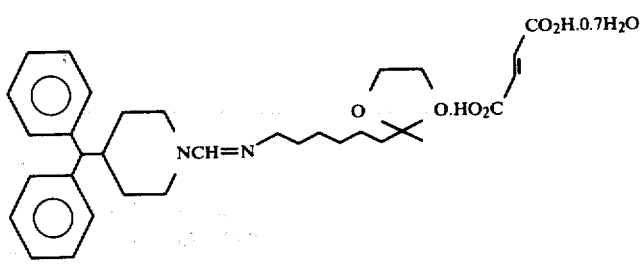

4-(Diphenylmethyl)-1-{{[6-(2-methyl-1,3-dioxolan-2-yl)hexyl]imino}methyl}piperidine (E)-2-Butenedioate (1:1) Hydrate (10:7) -McN-4980-46-98

A solution of 37.0 g (0.133 mole) of 1-formyl-4-(diphenylmethyl)piperidine in 165 ml of methylene chloride was treated with phosgene until evolution of gas ceased. The resulting solution was stripped, redissolved in methylene chloride, and stripped. The residue was dissolved in 165 ml methylene chloride, cooled to 0° and treated with a solution of 25.0 g (0.134 mole) of (2-methyl-1,3-dioxolan-2-yl)hexylamine followed by 52.50 g of anhydrous potassium carbonate. The mixture was stirred 4 hours at 25°, filtered, made basic with 3 N NaOH solution and the organic layer separated, dried over potassium carbonate, filtered, and stripped to give an orange oil. This material was passed through neutral alumina using ether as the eluant to give a yellow oil which was rechromatographed under the same conditions affording 27.65 g of clear oil, 99% pure by gc (SE-30, 90°–280°@16°/min). The fumarate salt was prepared from 3.78 g of this material to give 1.15 g (24%) of white solid (recrystallized from i-propanol), m.p. (sinter 143°) 145.5°–148.5° (Hoover).

Anal. Calc'd for $C_{29}H_{40}N_2O_2.C_4H_4O_4.0.7$ $H_2O$: C, 68.65; H, 7.92; N, 4.85; $H_2O$, 2.18. Found: C, 68.75; H, 7.87; N, 4.96; $H_2O$, 2.16.

EXAMPLE 2

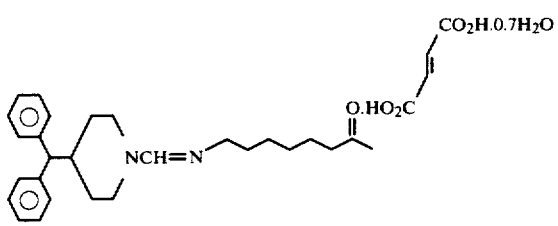

4-(Diphenylmethyl)-1-{[(7-oxooctyl)imino]methyl}-piperidine (E)-2-Butenedioate (1:1) Hydrate (10:7), McN-4955-46-98

A solution of the free base of 4-(diphenylmethyl)-1-{{[6-(2-methyl-1,3-dioxolan-2-yl)hexyl]imino}methyl}-piperidine, prepared from 14.20 g (0.032 m) of its fumarate salt, 24 ml of 70–72% perchloric acid, 24 ml of water and 100 ml of THF was allowed to stand at 25° for three hours. The THF was stripped and the residue was slurried with 3 N NaOH and $CH_2Cl_2$ until basic. The organic layer was separated, dried over anhydrous $K_2CO_3$, filtered, and stripped. The resulting oil was passed through neutral alumina using $CHCl_3$ as an eluant. There was isolated 4.42 g of clear oil, 98% pure by gc. This material was converted to the fumarate salt in isopropanol and recrystallized from isopropanol/acetone to give 2.85 g (17%) white solid m.p. 125.5°–128° (Hoover) after drying at 25° in vacuo overnight and equilibrating with atmosphere.

Anal. Calc'd for $C_{27}H_{36}N_2O.C_4O_4.0.7$ $H_2O$: C, 69.82; H, 7.88; N, 5.25; $H_2O$, 2.36. Found: C, 70.17; H, 7.86; N, 5.28; $H_2O$, 2.53.

EXAMPLE 3

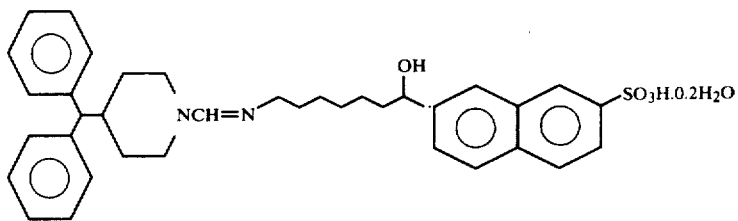

4-(Diphenylmethyl)-1-{[(7-hydroxyoctyl)imino]methyl}piperidine 2-Naphthalenesulfonate (1:1) Hydrate (4:1), McN-4978-71-98

To a slurry of 0.25 g (0.0055 mole) of sodium borohydride in 25 ml isopropanol at 0° was slowly added 5.00 g (0.012 mole) of 4-(diphenyl methyl)-1-{[(7-oxooctyl)imino]methyl}piperidine in 5 ml of isopropanol. The reaction was stirred 1.5 hours and treated with 40 ml of water. The resulting mixture was extracted with methylene chloride and the organic layer was separated, dried over anhydrous potassium carbonate, filtered and stripped to give 4.75 g of clear oil, 55% by gc. This material was dissolved in acetone and treated with 1.70 g of 2-naphthalenesulfonic acid followed by a small amount of ether to give a white solid. Subsequent recrystallizations from acetone-ethyl acetate and methyl ethyl ketone afforded 1.50 g (20%) of white solid, which after drying in vacuo at 70°, melted 129.5–132.5 (Hoover).

Anal. Calc'd for $C_{27}H_{38}N_2O.C_{10}H_8SO_3.0.25$ $H_2O$; C, 71.75; H, 7.56; N, 4.52; $H_2O$, 0.72. Found: C, 71.86; H, 7.72; N, 4.62; $H_2O$, 0.83.

EXAMPLE 4

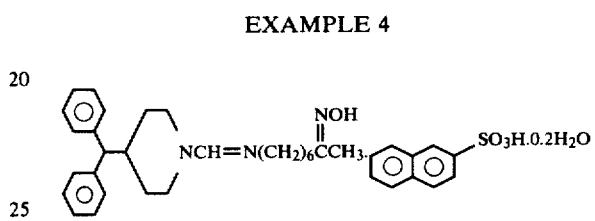

4-(Diphenylmethyl)-1-{{[7-(hydroxyimino)octyl]imino}methyl}piperidine 2-Naphthalenesulfonate (1:1) Hydrate (5:1), McN-5085-71-98

A solution of 3.00 g (0.0058 mole) of 4-(diphenylmethyl)-1-{[(7-oxooctyl)imino]methyl}piperidine sulfate (1:1) Hydrate (10:7), 0.48 g (0.0069 mole) of hydroxylamine hydrochloride and 15 ml of 95% ethanol was stirred two hours at 25°, stripped, and the residue basified in $CH_2Cl_2$ with 3 N NaOH solution. The organic layer was separated, dried over anhydrous $Na_2SO_4$, filtered, and stripped to an oil. This material was dissolved in acetone and treated with 2-naphthalenesulfonic acid. A solid was filtered off and recrystallized from acetone to give 1.41 g (39%) of white solid, m.p. (sinter 123°) 125°–128° (Hoover).

Anal. Calc'd for $C_{27}H_{37}N_3O.C_{10}H_8SO_3.0.2$ $H_2O$: C, 70.38; H, 7.24; N, 6.65; $H_2O$, 0.57. Found: C, 70.30; H, 7.27; N, 6.56; $H_2O$, 0.75.

EXAMPLE 5

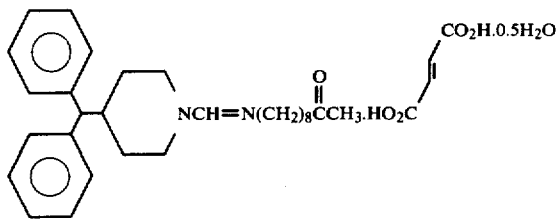

5-(Diphenylmethyl)-1-{[(9-oxodecyl)imino]methyl}-piperidine (E)-2-butenedioate (1:1) Hydrate (2:1), McN-5066-46-98

A solution of 2.76 g (0.006 mole) of 4-(diphenylmethyl)-1-{{[8-(2-methyl-1,3-dioxolan-2-yl)octyl]imino}-methyl}piperidine, 4.35 ml of 70–72% perchloric acid, 4.35 ml of water, and 20 ml of THF was allowed to stand at 25° for 3 hours. The solution was stripped, the residue dissolved in $CH_2Cl_2$ and made basic with 3 N NaOH solution. The organic layer was separated, dried over anhydrous $K_2CO_3$, filtered and stripped. The fumarate salt of this residue was prepared and recrystallized from ethanol-acetone, acetonitrile, and i-propanol-ether to give a solid, m.p. 108°–118°. This material was slurried in $CH_2Cl_2$, treated with 3 N NaOH solution until basic, the organic layer separated, dried over anhydrous $K_2CO_3$, filtered and stripped. Chromatography of the residue through neutral alumina ($CHCl_3$ eluant) gave 0.71 g of oil. The fumarate salt of this material was prepared and recrystallized twice from i-propanol-ether to give 0.34 g (10%) of white solid m.p. (sinter 100°) 118.5°–122° (Hoover).

Anal. Calc'd for $C_{29}H_{40}N_2O \cdot C_4H_4O_4 \cdot 0.5\ H_2O$: C, 71.07; H, 8.13; N, 5.02; $H_2O$, 1.61. Found: C, 70.80; H, 7.99; N, 5.07; $H_2O$, 1.41.

EXAMPLE 6

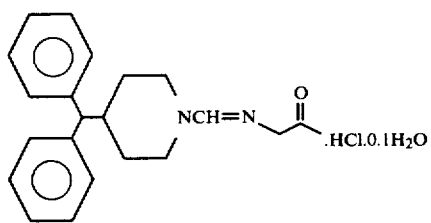

4-Diphenylmethyl-1-[(2-oxopropyl)imino]methyl piperidine Hydrochloride (1:1) Hydrate (10:1)-McN-5020-11-98

A mixture of 17.40 g (0.046 mole) of 4-(diphenylmethyl)-1-{{[(2-methyl-1,3-dioxolan-2-yl)methyl]imino}-methyl}piperidine, 38 ml of 70–72% perchloric acid, 38 ml of water and 165 ml of THF was allowed to stand at 25° for three hours. The THF was stripped and the aqueous residue made basic with 300 ml of 3 N NaOH solution at 0°. The resulting mixture was extracted with methylene chloride, the organic layer separated, dried over anhydrous potassium carbonate, filtered and stripped to a yellow-orange oil. This material was dissolved in ether, filtered through diatomaceous earth and treated with ethereal HCl until acidic. The resulting copious precipitate was filtered and recrystallized twice from ethanol-acetone to give 6.30 g (37%) of white solid, m.p. (darken sl at 215°) 221°–223.5° (Hoover).

Anal. Calc'd for $C_{22}H_{26}N_2O \cdot HCl \cdot 0.1\ H_2O$: C, 70.89; H, 7.36; N, 7.52; $H_2O$, 0.48. Found: C, 70.86; H, 7.42; N, 7.56; $H_2O$, 0.36.

EXAMPLE 7

Using the procedure described in Example 1, the following amidines may be prepared:

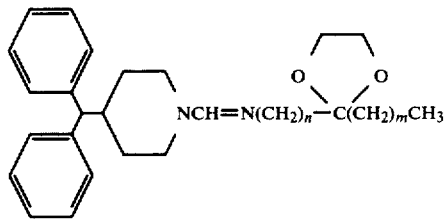

| n | m |
|---|---|
| 6 | 4 |
| 5 | 3 |
| 4 | 2 |
| 3 | 1 |
| 10 | 0 |
| 9 | 0 |
| 7 | 0 |
| 5 | 0 |
| 4 | 0 |
| 3 | 0 |
| 1 | 6 |
| 1 | 5 |
| 1 | 3 |

EXAMPLE 8

Using the procedure described in Example 2, the following keto amidines can be prepared:

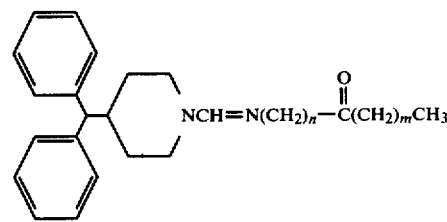

| n | m |
|---|---|
| 5 | 4 |
| 4 | 3 |
| 3 | 2 |
| 2 | 1 |
| 9 | 0 |
| 7 | 0 |
| 5 | 0 |
| 4 | 0 |
| 3 | 0 |
| 1 | 6 |
| 1 | 5 |
| 1 | 3 |

EXAMPLE 9

Using the procedure described in Example 3, the following alcohols can be prepared:

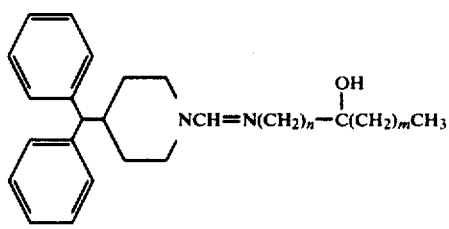

| n  | m |
|----|---|
| 6  | 4 |
| 5  | 3 |
| 4  | 2 |
| 3  | 1 |
| 10 | 0 |
| 9  | 0 |
| 8  | 0 |
| 7  | 0 |
| 5  | 0 |
| 4  | 0 |
| 3  | 0 |
| 1  | 6 |
| 1  | 5 |
| 1  | 3 |
| 1  | 0 |

EXAMPLE 10

Using the procedure described in Example 4, the following oximes can be prepared:

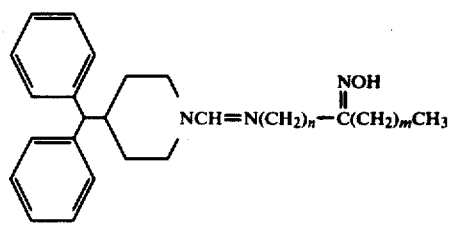

| n  | m |
|----|---|
| 6  | 4 |
| 5  | 3 |
| 4  | 2 |
| 3  | 1 |
| 10 | 0 |
| 9  | 0 |
| 8  | 0 |
| 7  | 0 |
| 5  | 0 |
| 4  | 0 |
| 3  | 0 |
| 1  | 6 |
| 1  | 5 |
| 1  | 3 |
| 1  | 0 |

EXAMPLE 11

Using the procedure described in Example 1, but substituting the aminoketals described in Preparation 10 for (2-methyl-1,3-dioxolan-2-yl)hexylamine, the following may be synthesized:

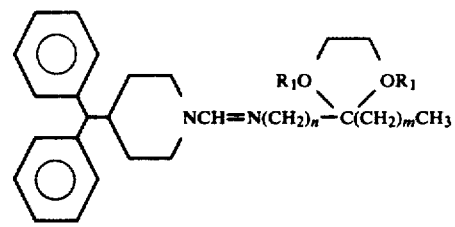

| n  | m | $R_1$       |
|----|---|-------------|
| 6  | 4 | $CH_3-$     |
| 5  | 3 | $CH_3-$     |
| 4  | 2 | $CH_3-$     |
| 3  | 1 | $CH_3-$     |
| 10 | 0 | $CH_3-$     |
| 9  | 0 | $CH_3-$     |
| 8  | 0 | $CH_3-$     |
| 7  | 0 | $CH_3-$     |
| 6  | 0 | $CH_3-$     |
| 5  | 0 | $CH_3-$     |
| 4  | 0 | $CH_3-$     |
| 3  | 0 | $CH_3-$     |
| 1  | 6 | $CH_3-$     |
| 1  | 5 | $CH_3-$     |
| 1  | 3 | $CH_3-$     |
| 1  | 0 | $CH_3-$     |
| 6  | 4 | $CH_3CH_2-$ |
| 5  | 3 | $CH_3CH_2-$ |
| 4  | 2 | $CH_3CH_2-$ |
| 3  | 1 | $CH_3CH_2-$ |
| 10 | 0 | $CH_3CH_2-$ |
| 9  | 0 | $CH_3CH_2-$ |
| 8  | 0 | $CH_3CH_2-$ |
| 7  | 0 | $CH_3CH_2-$ |
| 6  | 0 | $CH_3CH_2-$ |
| 5  | 0 | $CH_3CH_2-$ |
| 4  | 0 | $CH_3CH_2-$ |
| 3  | 0 | $CH_3CH_2-$ |
| 1  | 6 | $CH_3CH_2-$ |
| 1  | 5 | $CH_3CH_2-$ |
| 1  | 3 | $CH_3CH_2-$ |
| 1  | 0 | $CH_3CH_2-$ |

EXAMPLE 12

Following the procedure of Example 1, but replacing the (2-methyl-1,3-dioxolan-2-yl)hexylamine used therein with the compounds from Preparation 12, the following amidines may be prepared:

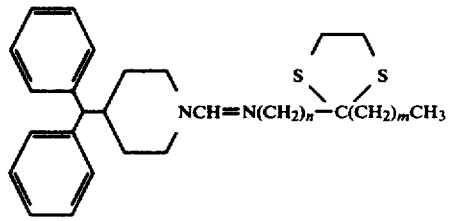

| n  | m |
|----|---|
| 6  | 4 |
| 5  | 3 |
| 4  | 2 |
| 3  | 1 |
| 1  | 0 |
| 10 | 0 |
| 9  | 0 |
| 8  | 0 |
| 7  | 0 |
| 6  | 0 |
| 5  | 0 |
| 4  | 0 |

-continued

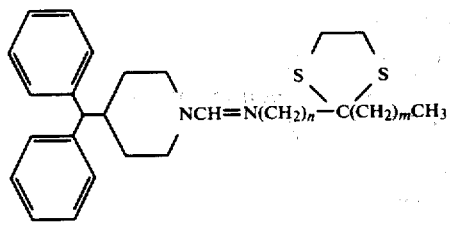

| n | m |
|---|---|
| 3 | 0 |
| 1 | 6 |
| 1 | 5 |
| 1 | 4 |
| 1 | 3 |

I claim:

1. 4-Diphenylmethyl-1-[(oxoalkyl)imino]methyl-piperidine or a derivative thereof of the formula:

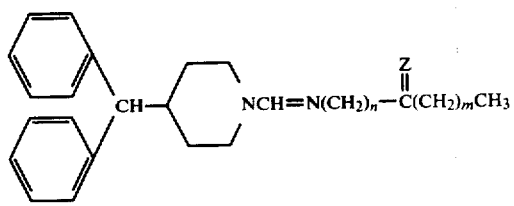
(II)

wherein:
n is an integer from 1-10, inclusive
m is an integer from 0-9, inclusive
n+m=1-10
Z is selected from the following:

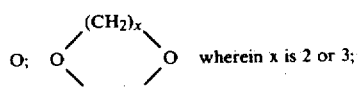
O;     wherein x is 2 or 3;

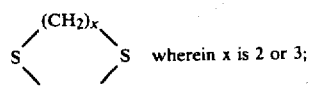
wherein x is 2 or 3;

-continued
$(OR_1)_2$ wherein $R_1$ is $C_{1-6}$ loweralkyl; NOH; and H,OH;

or a pharmaceutically acceptable acid addition salt thereof.

2. A compound according to claim 1 wherein in said formula
n is 1-10
m is 0-9
n+m=1-10
Z is O;

NOH; H,OH
and the pharmaceutically acceptable acid addition salts thereof.

3. A compound of claim 2 which is the free base or acid addition salt form of 4-(diphenylmethyl)-1-{[(7-oxooctyl)imino]methyl}piperidine.

4. A compund of claim 2 which is the free base or acid addition salt form of 4-(diphenylmethyl)-1-{[(7-hydroxyoctyl)imino]methyl}piperidine.

5. A compound of claim 2 which is the free base or acid addition salt form of 4-(diphenylmethyl)-1-{{[7-(hydroxyimino)octyl]imino}methyl}piperidine.

6. A compound of claim 2 which is the free base or acid addition salt form of 4-(diphenylmethyl)-1-{[(9-oxodecyl)imino]methyl}piperidine.

7. A compound of claim 2 which is the free base or acid addition salt form of 4-(diphenylmethyl)-1-[(2-oxopropyl)imino]methyl piperidine.

8. A compound of claim 2 which is the free base or acid addition salt form of 4-(diphenylmethyl)-1-{{[6-(2-methyl-1,3-dioxolan-2-yl)hexyl]imino}methyl}piperidine.

9. A pharmaceutical composition comprising an effective gastric acid secretion inhibiting amount of 4-diphenylmethyl-1-[(oxoalkyl)imino]methyl-piperidines and their derivatives compound of claim 1, in free base or acid addition salt form together with a pharmaceutically acceptable carrier.

10. A process of inhibiting gastric acid secretion in a mammal in need thereof by internally administering a pharmaceutical composition of claim 9.

* * * * *